United States Patent [19]
Van Hoeck et al.

[11] Patent Number: 5,423,818
[45] Date of Patent: * Jun. 13, 1995

[54] CLAMP FOR ATTACHING A VERTEBRAL FIXATION ELEMENT TO A SPINAL ROD

[75] Inventors: James E. Van Hoeck, Cordova; Michael C. Sherman, Memphis, both of Tenn.

[73] Assignee: Danek Medical, Inc., Memphis, Tenn.

[*] Notice: The portion of the term of this patent subsequent to Feb. 1, 2011 has been disclaimed.

[21] Appl. No.: 175,608

[22] Filed: Dec. 30, 1993

Related U.S. Application Data

[63] Continuation-in-part of Ser. No. 18,800, Feb. 17, 1993, Pat. No. 5,282,801.

[51] Int. Cl.⁶ .............................................. A61F 5/02
[52] U.S. Cl. ........................................ 606/61; 606/73; 606/72
[58] Field of Search ................ 606/60, 61, 72, 73, 606/62, 64; 623/17

[56] References Cited

U.S. PATENT DOCUMENTS

| | | | |
|---|---|---|---|
| 1,085,461 | 1/1914 | Michaelis . | |
| 2,391,693 | 12/1945 | Ettinger | 606/61 |
| 4,773,402 | 9/1988 | Asher et al. . | |
| 4,987,892 | 1/1991 | Krag et al. | 606/61 |
| 5,010,879 | 4/1991 | Moriya et al. . | |
| 5,053,034 | 10/1991 | Olerud | 606/61 |
| 5,122,131 | 6/1992 | Tsou | 606/61 |
| 5,176,678 | 1/1993 | Tsou | 606/61 |
| 5,201,734 | 4/1993 | Cozad et al. | 606/62 |
| 5,209,752 | 5/1993 | Ashman et al. | 606/61 |
| 5,246,442 | 9/1993 | Ashman et al. | 606/61 |
| 5,261,909 | 11/1993 | Sutterlin et al. | 606/61 |

FOREIGN PATENT DOCUMENTS 3219575 2/1988 Germany .............................. 606/61

Primary Examiner—Gary Jackson
Attorney, Agent, or Firm—Woodard, Emhardt, Naughton Moriarty & McNett

[57] ABSTRACT

A clamp is provided for clamping a spinal rod to a vertebral fixation element which permits access directly from the top of the instrumentation site. The clamp includes a body defining a channel configured to receive the spinal rod and a pair of conical sleeves for restrainably securing the spinal rod to the clamp by forcibly inserting the sleeves between the spinal rod and the channel. The clamp further includes a projection extending from the body, terminating in a T-bar, and a washer slidably disposed on the projection between the T-bar and channel. As the conical sleeves are forcibly inserted into the channel, the sleeves bear upon the the washer and displace the washer in the direction of the T-bar, thereby clamping the vertebral fixation element between the T-bar and washer. The dual function of the conical sleeves thereby clamps the spinal rod to a vertebral fixation element.

33 Claims, 6 Drawing Sheets

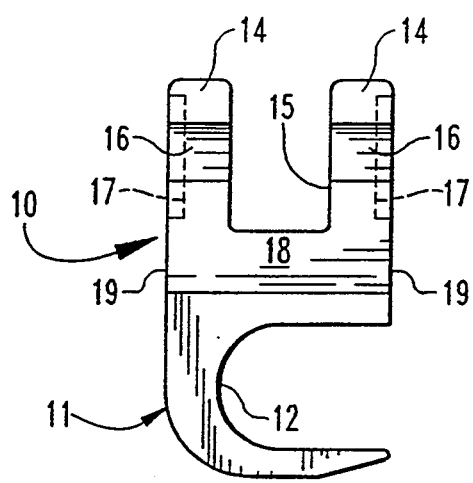
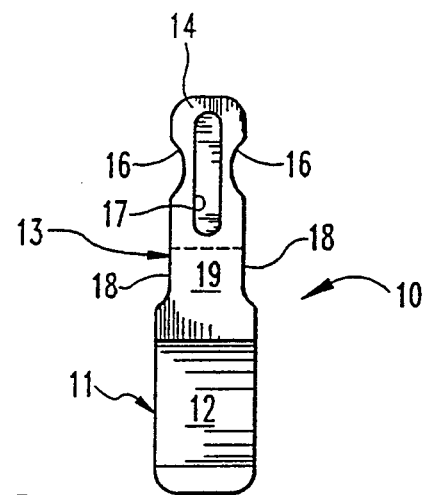
Fig. 3
Fig. 4
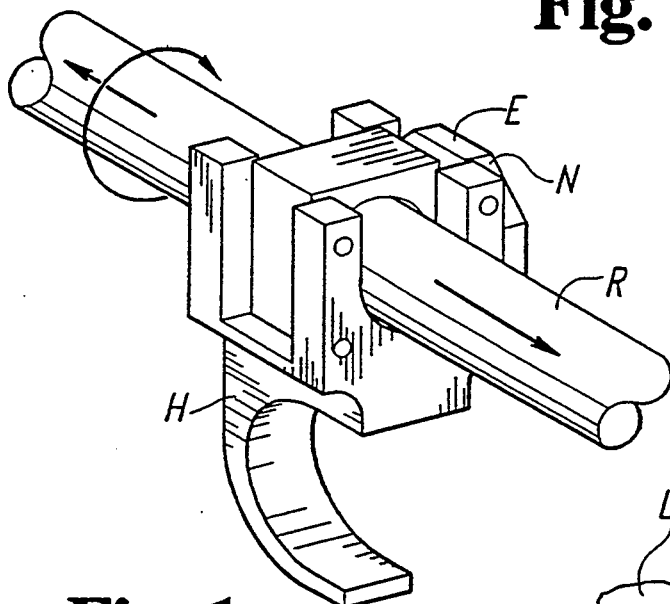
Fig. 1
(Prior Art)
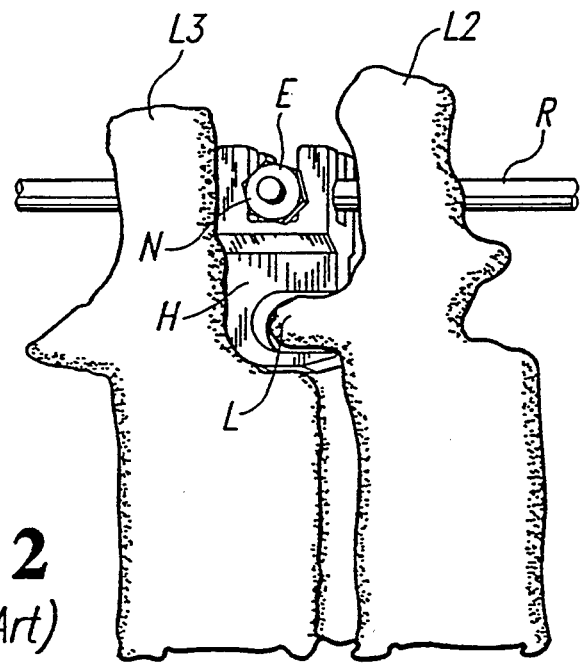
Fig. 2
(Prior Art)

CLAMP FOR ATTACHING A VERTEBRAL
FIXATION ELEMENT TO A SPINAL ROD

REFERENCE TO RELATED APPLICATIONS

This application is a continuation-in-part of U.S. patent application Ser. No. 08/018,800, filed on Feb. 17, 1993, now U.S. Pat. No. 5,282,801, and entitled TOP TIGHTENING CLAMP ASSEMBLY FOR A SPINAL FIXATION SYSTEM

BACKGROUND OF THE INVENTION

The present invention concerns spinal fixation systems, and particularly systems utilizing elongated rods adjacent the spinous process providing a base for connecting fixation elements to several vertebral levels. More specifically, the invention concerns improvements to the manner in which the vertebral fixation elements are engaged to the elongated spinal rod.

Several techniques and systems have been developed for correcting and stabilizing spinal curves and facilitating spinal fusion. In one system, a bendable rod is longitudinally disposed adjacent the vertebral column, or spinous process, and is fixed to various vertebrae along the length of the column by way of a number of fixation elements. A variety of fixation elements can be provided which are configured to engage specific portions of the vertebra. For instance, one such fixation element is a spinal compression/distraction hook. This type of spinal hook is used to anchor the rod by engaging the laminae of the vertebra. Another fixation element is a spinal screw, which includes cancellous threads for engagement within the pedicle of a vertebra.

An example of a rod-type spinal fixation system under consideration with the present invention is the TSRH ® spinal system sold by Danek Medical, Inc. In this system, a spinal hook, such as the hook H shown in FIG. 1 for example, is engaged to an elongated fixation rod R by way of an eyebolt assembly E. As is known in the art, the eyebolt E is mounted on the spinal rod and captured within yokes on the spinal hook. A nut N is then threaded onto a threaded post of the eyebolt to clamp the hook yoke between the nut and the fixation rod R. In this manner, the eyebolt E and the yokes of the hook H provide three degrees of fixation as represented by the arrows in FIG. 1. Details of the TSRH ® spinal implant system are disclosed in the "TSRH ® Surgical Technique Manual" provided by Danek Medical, Inc., published in 1990, which disclosure is incorporated herein by reference.

It is the goal of the surgeon using spinal implant systems such as the Danek TSRH ® system to apply vertebral fixation elements, such as a spinal hook or a bone screw, to the spine in appropriate anatomic positions, and then to engage each fixation element to the spinal rod. One problem with the spinal hooks H of the prior art, as represented in FIGS. 1 and 2, is that the hooks are rather bulky and wide since the fixation yokes of the hook were configured to surround the spinal rod R. Moreover, it had been found that hooks such as hook H only allow the rod to be implanted in one position relative to the spinal column as dictated by the required position of the shoe of the hook against the vertebra.

In order to address that and other problems with the prior art systems shown in FIGS. 1 and 2, new spinal fixation elements have been developed which are the subject of U.S. Pat. No. 5,246,442 entitled SPINAL HOOK and U.S. Pat. No. 5,261,909 entitled VARIABLE ANGLE SCREW, assigned to the assignee of the present invention. One such fixation element, a spinal hook 10, is shown in FIGS. 3 and 4, and includes a shoe 11 having a bone engaging surface 12. The bone engaging surface 12 can be formed in any known shape to engage a laminae of a vertebra, for instance. Integral with the shoe 11 is a top portion 13 that forms a pair of posts 14 disposed apart from each other in the form of a U-shaped yoke to define a slot 15 therebetween. The slot 15 is wide enough to receive an eyebolt assembly, such as eyebolt assembly E shown in FIGS. 1 and 2. A pair of coaxial grooves 16 formed in each lateral surface 18 of the hook 10 are each configured to receive a portion of a spinal rod, such as rod R shown in FIGS. 1 and 2. These rod grooves 16 are present on each lateral surface 18 of the posts 14 so that the hook 10 can be oriented on either side of a spinal rod. Slots 17 are provided on each end face 19 for engagement by a hook-holding insertion instrument.

Another newly developed vertebral fixation element is a variable angle spinal screw, which is the subject of a pending application assigned to the assignee of the present invention. Certain details of this novel variable angle screw system are shown in FIG. 10. In particular, the screw 70 includes a shank 71 having bone engaging or cancellous threads formed thereon. The screw 70 also includes an upper yoke 73 formed by a pair of posts which define a U-shaped slot opening 74 configured to engage a specially designed connector for connecting the screw 70 to a spinal rod. The screw 70 includes an interdigitating face 76 having a number of radial splines 77 formed thereon.

Leaving the details of these newly developed vertebral fixation elements to their respective pending applications, can be appreciated that the central post hook 10, of FIGS. 3 and 4, and the variable angle screw 70, of FIG. 10, have increased the versatility of rod-type spinal implant systems, such as the TSRH ® system provided by Danek Medical. However, one feature consistent between these newly developed fixation systems, as well as the prior art spinal hook H shown in FIG. 1, is that the eyebolt assembly E used to engage the fixation component to the spinal rod is "side-tightening". In other words, the threaded post of the eyebolt E and the nut N engaging the post both project laterally away from the spinal rod R, as specifically depicted in FIGS. 1 and 2. It has been found in practice that it is often cumbersome to engage the nut N with a wrench to tighten the nut onto the eyebolt assembly E. Moreover, simple mechanics dictates that the wrench can only be moved through a partial turn before the handle of the wrench contacts the surrounding tissue. This necessitates taking the wrench off of the nut and re-engaging it for an additional partial rotation. Ratchet type wrench systems are typically not acceptable in procedures of this sort because the lateral space required for the ratchet mechanism unnecessarily impinges on the surrounding tissue and requires greater space at the surgical site.

Spinal and orthopedic procedures are rapidly becoming prevalent surgeries, largely because of the high incidence of low back pain syndrome. In the past, surgical techniques for alleviating low back pain or for addressing spinal deformities or injuries has required fairly complicated and massive surgical techniques. The focus in recent times has been to greatly reduce the degree of invasion into the patient required for instrumenting a spine, as well as to reduce the amount of trauma to tissue surrounding the instrumentation, both during the procedure and after the spinal instrumentation has been implanted.

One cog in this worthwhile goal for minimally invasive spinal surgical techniques, is to provide an improved means for clamping the various vertebral fixation components to a spinal rod in situ. Such a system should eliminate the side-tightening requirement of prior art systems. In addition, such a system should retain the versatility achieved by newly developed central post hooks and variable angle screw fixation elements. It is the goal of the present invention to address this and other concerns.

SUMMARY OF THE INVENTION

The present invention contemplates a spinal fixation system for engagement to the spine of a patient between several vertebral levels, particularly utilizing an elongated spinal rod configured for placement adjacent the spine. The system includes a number of vertebral fixation elements, each including a vertebra engaging portion and a rod engaging portion. In accordance with the invention, the rod engaging portions are of the type having a pair of posts extending from the vertebra engaging portion, the posts defining a slot opening therebetween. Opposite lateral surfaces of the posts are configured to engage the spinal rod, particularly by way of coaxial grooves formed in each lateral surface. A top-loading clamp is provided for clamping the vertebral fixation element to the spinal rod to permit top tightening of the clamp onto the rod. The clamp includes a body defining an elongated bore configured to receive the spinal rod therethrough, and having a length along its longitudinal axis greater than the diameter of the spinal rod so that the rod can at least initially slide within the bore. The body further defines first and second threaded bores extending from opposite top and bottom surfaces of the body, both which intersect the elongated bore. A set screw is provided which can alternatively be threaded through either of the threaded bores and into the rod bore to bear against the spinal rod disposed within.

The top-loading clamp further includes a projection extending from the body generally parallel to the longitudinal axis of the elongated bore. THE projection terminates in a T-bar which is arranged generally parallel to the longitudinal axis of the spinal rod when the rod extends through the elongated bore. The T-bar has a clamping surface directed inwardly toward the elongated bore that is configured to engage the lateral surfaces of each of the pair of posts of the vertebral fixation element.

The top-loading clamp provides means for clamping the posts of the vertebral fixation element to the spinal rod. Specifically, both the rod and the fixation element are clamped between the set screw and the clamping surface of the T-bar as the set screw is threaded further into the rod bore. The clamp of the present invention provides this means for clamping the components together while permitting top-tightening of the system, that is directly above the instrumentation site rather than laterally relative to the spinal rod.

In one embodiment, the vertebral fixation element is a spinal hook. In another embodiment, the fixation element is a variable angle screw having radial splines on one face of the rod engaging portion of the screw. In this embodiment, the top-loading clamp includes a washer having a first surface configured to engage the spinal rod, and an opposite second surface which includes a plurality of radial splines adapted for interdigitating engagement with the radial splines of the variable angle screw. The washer includes an opening therethrough configured to permit insertion of the washer over the T-bar. The washer is slidably mounted over a hub of the body, which is staked to keep the washer from sliding off the hub. In this embodiment, the washer is disposed between the vertebral fixation element and the spinal rod and is clamped therebetween when the set screw bears against the spinal rod. The interdigitating splines prevent rotation of the vertebral fixation element about the projection.

The present invention further contemplates an alternate clamping arrangement for clamping the spinal rod to a variable angle screw. This alternate clamping arrangement includes a body defining a channel configured to receive the spinal rod therein, and having a length along its longitudinal axis greater than the diameter of the spinal rod so that the rod may be disposed within the channel with a predetermined play. The channel is further configured to be tapered from each of its opposing ends towards the center. As with the previous embodiment, a washer is provided having a first surface configured to engage the spinal rod, and an opposite second surface which includes a plurality of radial splines adapted for interdigitating engagement with the radial splines of a variable angle screw. The washer further includes an opening therethrough configured to permit insertion of the washer over the T-bar and is slidably mounted over a hub of the body, which is staked to keep the washer from sliding off the hub. In this embodiment, a pair of conical sleeves are provided, each having a split through the sleeve and extending the length of the sleeve, and a bore therethrough sized to slidably receive the spinal rod. The washer is disposed between the variable angle screw and the spinal rod and is clamped therebetween when the conical sleeves are inserted into the tapered passages of the channel to form a force fit between the two sets of tapered surfaces, thereby fixing the variable angle screw to the spinal rod. Each of the conical sleeves is provided with a recess groove configured to receive a sleeve removing tool therein for sliding the sleeves out of the tapered channel so that the clamp may be repositioned. This embodiment can be modified to permit the conical sleeve attachment of a spinal rod to a spinal hook.

The top-loading clamp of the present invention provides the significant advantage of allowing the clamping mechanism to be tightened from directly above the instrumentation site. The two threaded bores allow the clamp to be oriented on either side of a spinal rod, as necessary to mate with a vertebral fixation element already engaged to a vertebra. The conical sleeve attachment further eliminates the need for wrenches or ratchets by providing a clamping structure that requires only a single instrument to compress the sleeves into the clamp in order to achieve final fixation of the spinal rod to the variable angle screw or spinal hook. Other advantages and benefits of the present invention can be discerned from the following written description and accompanying figures.

DESCRIPTION OF THE FIGURES

FIG. 1 shows a spinal hook of known design engaged to a fixation rod by way of an eyebolt assembly, as configured in accordance with one prior art system, the TSRH® spinal system.

FIG. 2 is a side view showing the system depicted in FIG. 1 in which a standard hook is engaged about the laminae of a lumbar vertebra.

FIG. 3 is a side elevational view of the spinal hook of recent design for which the top-tightening clamp assembly of the present invention is adapted to engage.

FIG. 4 is an end elevational view of the spinal hook shown in FIG. 3.

DESCRIPTION OF THE PREFERRED EMBODIMENTS

Figure 7:
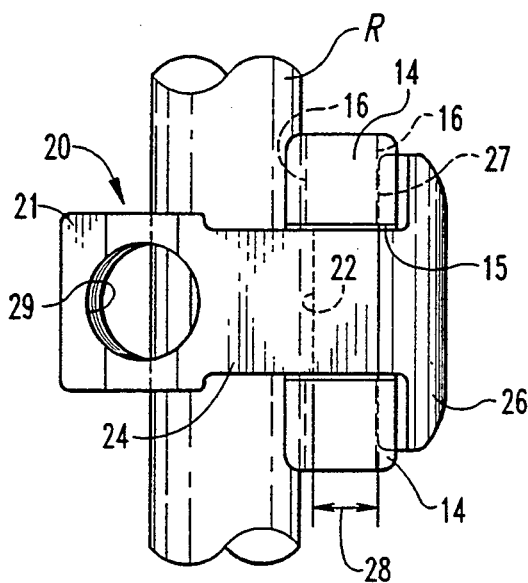
FIG. 7 is a top elevational view of the assembly shown in FIG. 5.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 10:
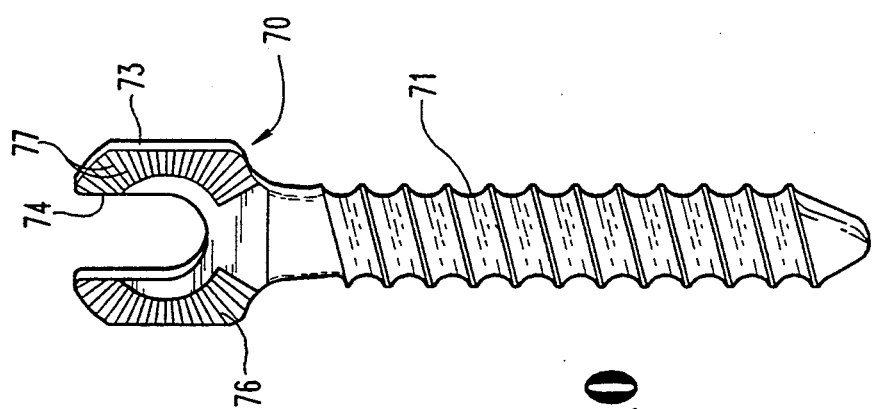
FIG. 10 shows a variable angle spinal screw for use with the top-tightening clamp assembly depicted in FIGS. 8 and 9.

As discussed in the background of the invention, the present invention in the preferred embodiment, contemplates a clamp assembly adapted to engage a newly developed spinal hook of the type shown in FIGS. 3 and 4, or a newly developed variable angle screw of the type shown in FIG. 10. However, it is understood that other hook and bone screw configurations are contemplated for use with the clamp assembly of this invention. The clamp assembly of the preferred embodiment is specifically adapted to engage these vertebral fixation elements to an elongated spinal rod.

Figure 5:
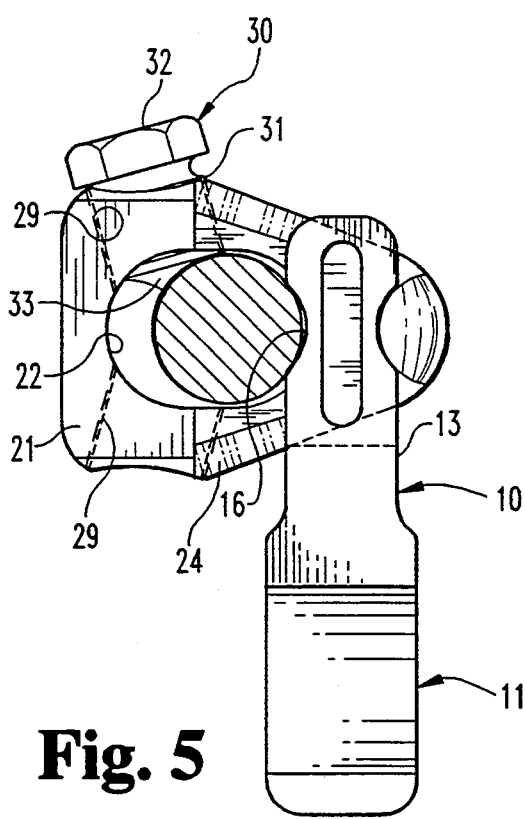
FIG. 5 is an end elevational, partial cross sectional, view of a top-tightening clamp assembly in accordance with one embodiment of the present invention, shown clamping a spinal hook of the type shown in FIG. 4 to a spinal rod.
Figure 6:
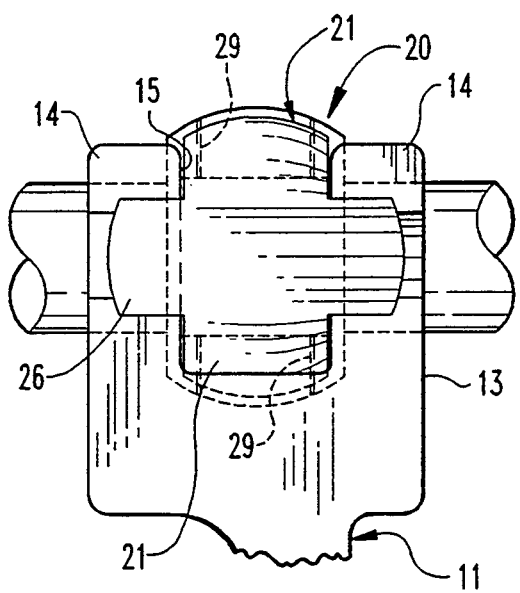
FIG. 6 is a side elevational view of the assembly shown in FIG. 5.

In accordance with one embodiment of the invention, a top-tightening clamp assembly 20 is provided, as shown in FIGS. 5-7. The assembly 20 includes a clamp body 21, which is preferably formed of a biocompatible metal such as titanium or stainless steel. The clamp body 21 defines a rod bore 22 through which a spinal rod, such as rod R, extends. It will be noticed from FIG. 5 that the rod bore 22 is elongated so that the spinal rod R can move, at least initially, within the bore along a longitudinal axis of the bore transverse to the longitudinal axis of the spinal rod R. In one specific embodiment adapted for use with a ¼" spinal rod, the length of the bore along its longitudinal axis is 0.351 inches. The ends of the rod bore are formed at a radius that is slightly larger than the diameter of the spinal rod.

The clamp body 21 includes a projection 24 extending laterally therefrom relative to the spinal rod once the clamp assembly 20 is engaged within the patient. The projection 24 extends generally parallel to the longitudinal axis of the rod bore 22 and terminates in a T-bar 26, so named because the bar 26 combined with the projection 24 are in the shape of a "T", with the T-bar arranged generally parallel to the longitudinal axis of the spinal rod R extending through the rod bore 22. The T-bar includes an inwardly facing surface 27 that is convexly curved toward the rod bore. Reference to the direction "inward" in connection with this invention is intended to mean facing toward the rod bore 22 and the spinal rod R within.

The clamp body 21 is particularly designed so that the distance between the curved inward surface 27 of the T-bar 26 and the closest point of the rod bore 22 is less than the width of a vertebral fixation element to be clamped to the rod. In the preferred embodiment, this fixation element is the central post hook 10 as previously described and as depicted most clearly in FIG. 5. Consequently, the distance, labeled 28 in FIGS. 5 and 7, between the innermost point on the curved inward surface 27 and the nearest point of the rod bore 22 is narrower than the width of the post 14 of the hook 10. In this manner, the spinal rod R can contact the groove 16 on one side of the spinal hook 10, without first striking the end of the rod bore 22. As shown in FIG. 5, the clamp assembly 20 contemplates that the spinal hook 10 will be firmly engaged between a spinal rod R and the inward surface 27 of the T-bar 26. The surface 27 of the T-bar is configured to mate with one of the coaxial grooves 16 in the post 14 of the spinal hook 10. For engaging one specific spinal hook, the distance 28 is 0.110 inches.

The clamp body 21 further defines a pair of threaded bores 29, each projecting inwardly from opposite sides of the body toward the rod bore 22, and in fact intersecting the rod bore. Each of the threaded bores 29 is adapted to receive a set screw 30 threaded therein. The set screw 30 includes a threaded stem 31 having threads for mating with the threads of the bores 29, and a driving head 32 which can assume a variety of configurations. In FIG. 5, the driving head 32 is configured to accept a standard socket wrench, although the driving head 32 can be alternatively configured to receive an allen head wrench. At the distal end of the threaded stem 31 is a contoured tip 33 adapted to engage the surface of a spinal rod R. Preferably, the tip 33 is formed in a spherically conical shape, as depicted in FIG. 5, to provide a line contact with the rod along the curvature of the tip. In one specific embodiment, the tip 33 is formed at a 0.115 inch radius to engage a ¼ inch spinal rod. Alternatively, the hip 33 may also be rounded or blunt, thereby providing essentially a point contact with the spinal rod.

With the spherically conical shaped tip 33, it is preferred that the threaded bore 52 intersect the rod bore 22 at a non-perpendicular angle to the longitudinal axis of the bore. Preferably, this bore 52 intersects the rod bore 22 at an angle between 60° and 90°. In the specific embodiment shown in FIG. 5, the threaded bore 52 intersects the rod bore 22 at an angle of 74.5°. This angle allows a firm contact between the tip 33 of the set screw and the spinal rod R, while also keeping the driving head 32 accessible from the top of the implanted construct.

With the foregoing description accompanied by FIGS. 5-7, the manner of using the clamp assembly 20 of the present invention may be clear to one of ordinary skill in the art. Specifically, in accordance with known spinal rod instrumentation procedures, a fixation element, such as hook 10 is first positioned in contact with a vertebra to be instrumented. The spinal rod R is then positioned appropriately to provide purchase for engagement with the hook 10. Alternatively, the spinal rod R can already be positioned rigidly at its ends or at various locations along the rod at several vertebral levels. In this instance, an additional spinal hook would be added subsequent to the positioning of the spinal rod and the clamp assembly 20 would be used to engage the hook to the rod. In either approach, it is important that the clamp assembly 20 already be situated on the spinal rod, that is with the rod R threaded through the rod bore 22, prior to introduction of the rod into the patient. The set screw 30 is initially loosely threaded into one of the threaded bores 29 so that there is adequate free play between the spinal rod and the walls of the bore 22. In addition, the clamp assembly 20 is permitted to slide longitudinally along the length of the spinal rod to the location of the hook to be engaged to the rod.

Once the clamp assembly 20 is positioned adjacent the spinal hook 10, the hook is situated with the opposite posts 14 straddling the projection 24—that is, with the projection 24 extending through the slot 15 in the spinal hook 10, as shown in FIGS. 6 and 7. The clamp assembly 20 can be manipulated so that the curved inward surface 27 of the T-bar 26 engages a groove 16 in one lateral surface 18 of the hook. Once the clamp assembly 20 is properly oriented between the spinal rod R and the fixation hook 10, the set screw 30 is then tightened within the threaded bore 29 so that the contoured tip 33 contacts and presses the spinal rod R against: a groove 16 of the hook 10, Preferably, the set screw 30 is threaded into the bore as far as possible, finger tight. It has been found that this provides adequate engagement to clamp the spinal rod to the fixation element or hook 10 by way of the clamp assembly 20.

The clamp assembly 20, and particularly the clamp body 21, is provided with a pair of opposite threaded bores 29 to increase the versatility of the assembly of the present invention. Since the clamp body 21 must be pre-engaged on the spinal rod, it is possible that the hook to be clamped to the rod will be situated on one side or the other of the rod once the rod has been bent and/or rotated into position. For example, the hook 10 is shown engaged on the right side of the rod R in FIG. 5. However, once the entire spine has been instrumented it can be discovered that the hook will actually reside on the left side of the rod R. In this instance, it is absolutely essential that the clamp assembly 20 be capable of altering its orientation to engage the left-side located spinal hook. Consequently, in this instance the clamp body 21 need only be rotated about the spinal rod R so that the T-bar 26 projects to the left of the spinal rod (as viewed in FIG. 5) and what had been the lowermost bore 29 is now facing upward to receive a set screw 30 wherein. Most preferably, the clamp body 21 is symmetric about the longitudinal axis of the rod bore 22.

In this embodiment, the fixation element is a hook 10 having a top portion 13 in a central post configuration. It is understood, of course, that a bone screw can be provided in the central post configuration. The engagement of the central post screw to the rod can be readily accomplished using the clamp assembly 20.

Figure 9:
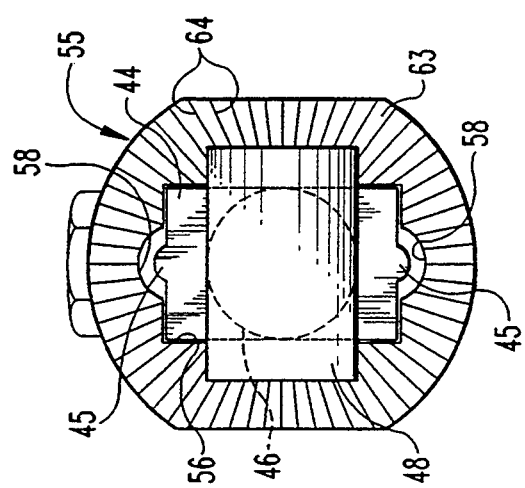
FIG. 9 is a side elevational view of the alternative embodiment shown in FIG. 8.
Figure 8:
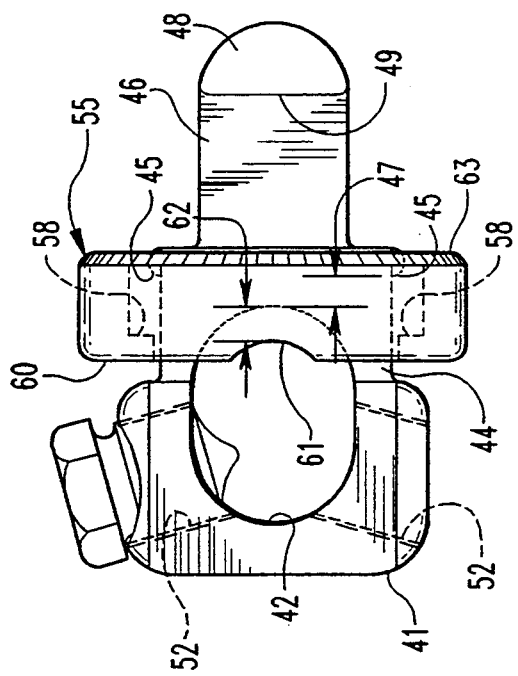
FIG. 8 shows an alternative embodiment of a top-tightening clamp assembly for use with a variable angle screw.

The present invention is also readily adapted for engagement with a variable angle screw, such as the screw 70 depicted in FIG. 10. One alternative embodiment of the invention is shown in FIGS. 8 and 9. It is understood of course that this alternative embodiment is configured to engage a spinal rod just as the embodiment shown in FIGS. 5-7. However, for clarity the spinal rod and the specific location of the variable angle screw has been omitted from the figures.

In the alternative embodiment of FIGS. 8 and 9, a clamp assembly 40 includes a clamp body 41 which defines a rod bore 42, which is for all intents substantially identical to the same features on the clamp body 21 in FIG. 5. However, in a modification from the previous embodiment, the clamp body 41 defines a hub 44, from which a circular projection 46 extends. The hub 44 in the preferred embodiment is generally rectangular in shape, as shown in FIG. 9. A T-bar 48 is formed at the end of the projection 46. In a further modification from the previous embodiment, the T-bar 48 does not include a curved inward surface, but instead has a flat inward surface 49 facing toward the rod bore 42. As with the previous embodiment, the clamp body 41 defines opposite threaded inwardly opening bores 52 which are adapted to engage set screws 53.

The clamp assembly 40 further includes an interdigitating washer 55. The washer 55 includes an opening 56 which is configured similar to the hub 44 both dimensionally and in its shape. The opening 56 and the hub 44 have almost identical dimensions so that the washer 55 can be passed onto the hub 44. In order to facilitate retaining the washer 55 on the hub, the washer includes a pair of staking recesses 58 shown in FIGS. 8 and 9. The staking recesses 58 each receive a staked portion 45 of the hub 44 so that the washer cannot slide off the hub.

A staking tool can be used to depress the hub 44 to form the staked portions 45 when the washer is situated on the hub. It is understood that this staking operation is done prior to implanting the assembly 40 within the patient, or engaging it onto the spinal rod.

In order to allow the washer 55 to be received on the hub, it is important that the T-bar 48 be similarly shaped but slightly smaller than the opening 56 in the washer. The washer 55 can then be passed over the T-bar 48 and rotated so that the opening 56 is oriented perpendicular to the axis of the T-bar 48, as shown in FIG. 9.

Once staked onto the hub 44, the washer 55 can slide along the hub between the body 41 and the staked portions 45. It is contemplated that the free-play of the washer at its thinnest point on the rod groove 61 and the staking recesses 58 (denoted 62 in FIG. 8), is greater than the distance between the end of the rod bore 42 and the staked portions 45 (denoted 47 in FIG. 8). This dimensional relationship ensures that the spinal rod has room to engage the rod groove 61 of the washer 55 before contacting the end of the rod bore 42 when clamped by the set screw 53.

In one important feature of this embodiment, the washer 55 includes a rod face 60 which is directed toward the rod bore 42. The rod face 60 defines a groove 61 for receiving a spinal rod therein, in the manner shown in FIG. 5. The washer 55 further includes an opposite outward face 63 which incorporates the interdigitating feature of the invention. Specifically, the outward face 63 includes several radial splines 64 formed thereon. These radial splines are configured comparably with the radial splines 77 on the variable angle screw 70. The projection 46 is circular in cross section so that the variable angle screw 70 can be rotated relative to the projection about its U-shaped slot 74. Thus, the clamp assembly 40 of this embodiment is well suited for receiving a variable angle screw 70 that is engaged into the pedicle of the vertebra, for instance, at a non-vertical angle (that is angled in the plane of the spinous process).

Figure 12:
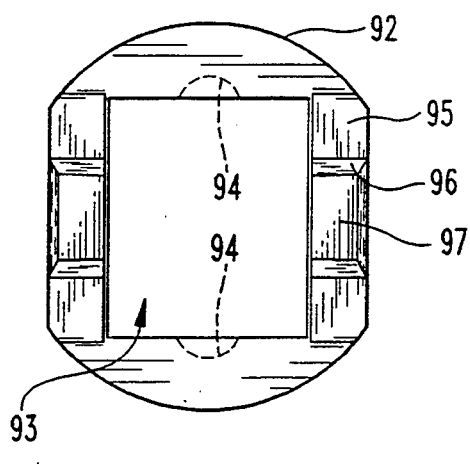
FIG. 12 is a side elevational view of the rod engaging surface of the washer of the clamp assembly shown in FIG. 11.
Figure 11:
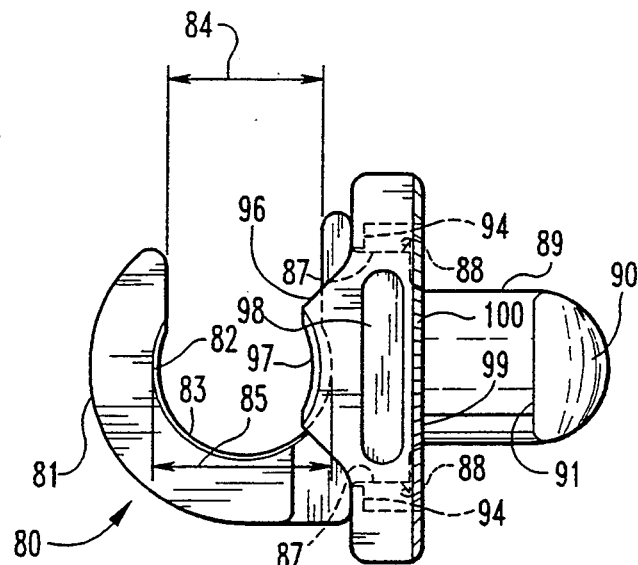
FIG. 11 is a top-loading clamp assembly for use with a variable angle screw and conical rod attachment sleeves, in accordance with another embodiment of the present invention.
Figure 15:
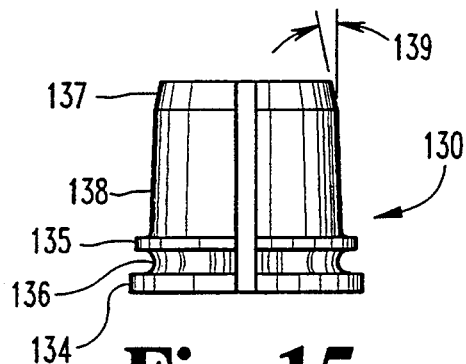
FIG. 15 is a bottom elevational view of another embodiment of a conical attachment sleeve *to be used with the clamp assembly of FIG. 11.
Figure 16:
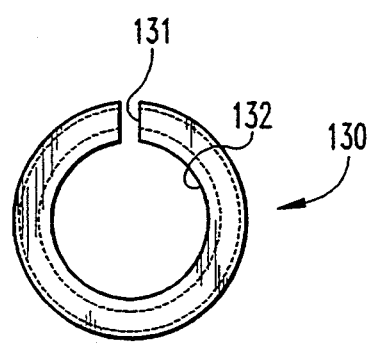
FIG. 16 is an end elevational view of the conical sleeve shown in FIG. 15.
Figure 17:
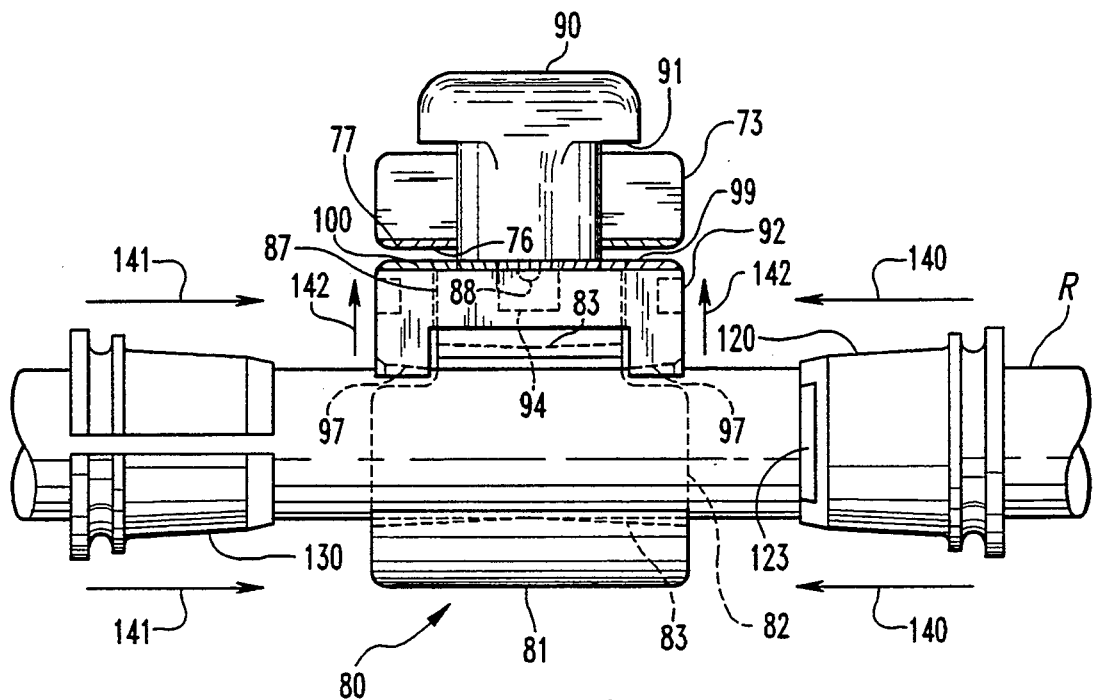
FIG. 17 is a top elevational view of the clamp assembly of FIG. 11, shown with a variable angle screw and spinal rod prior to clamping by insertion of the conical sleeves into the clamp channel.

A further embodiment of the invention for engagement with a variable angle screw 70 is shown in FIGS. 11 through 18. Referring specifically to FIGS. 11, 12, and 17, a clamp assembly 80 includes a clamp body 81 which defines a rod channel 82 for receiving a spinal rod, such as rod R shown in FIGS. 5 through 7. Channel opening 84 is sized so that clamp assembly 80 may be top loaded onto Rod R. Rod channel 82 is sized so that the spinal rod R can move, at least initially, with a predetermined play within the channel. Rod channel 82 is further configured to be tapered from each of the opposing channel ends-towards it center as shown at portion (FIG. 17) 83. In one specific embodiment adapted for use with a one quarter inch rod, channel opening 84 is 0.256 inches, the width of a channel 85 along its transverse axis at its two opposing ends is 0.2983 inches and the portion 83 is tapered at 4° increasing from the center of channel 82 toward its opposing ends in either direction.

The clamp body 81 includes a hub 87 from which a projection 89 extends laterally therefrom. The hub 87 in the preferred embodiment is generally rectangular in shape as shown in FIG. 11. The projection 89 extends generally perpendicular to the longitudinal axis of the rod channel 82 and terminates in a T-bar 90. T-bar 90 can be configured identically to T-bar 46 of the previous embodiment, being arranged generally parallel to the longitudinal axis of the spinal rod R in the rod channel 82. The T-bar 90 includes a flat inward surface 91 facing toward the rod channel 82.

As with the previous embodiment, clamp assembly 80 further includes an interdigitating washer 92, defining a rectangular opening 93 therethrough which is configured similar to hub 87, both dimensionally and in its shape. The opening 93 is sized slightly larger than the hub 87 so that the washer 92 can be passed onto the hub 87. The T-bar 90 is also similarly shaped but slightly smaller than the largest dimension of opening 93 so that the washer 92 can be passed over the T-bar 90. The washer opening 93 preferably has a smaller dimension that is smaller than the T-bar length. The washer can then be rotated on the projection 89 so that the opening 93 is oriented perpendicularly to the axis of the T-bar 90, as shown in FIG. 9 for the previous embodiment. In order to keep the washer 92 from sliding along the hub 87 toward the T-bar 90, a pair of staking recesses 94 are provided within the washer 92. Staking recesses 94 contact staked portions 88 of the hub 87 as washer 92 is moved a predetermined distance toward the T-bar 90, thereby preventing the washer 92 from sliding off the hub 87. A staking operation identical to that described in the previous embodiment is performed to provide the staked portions 88.

Figure 18:
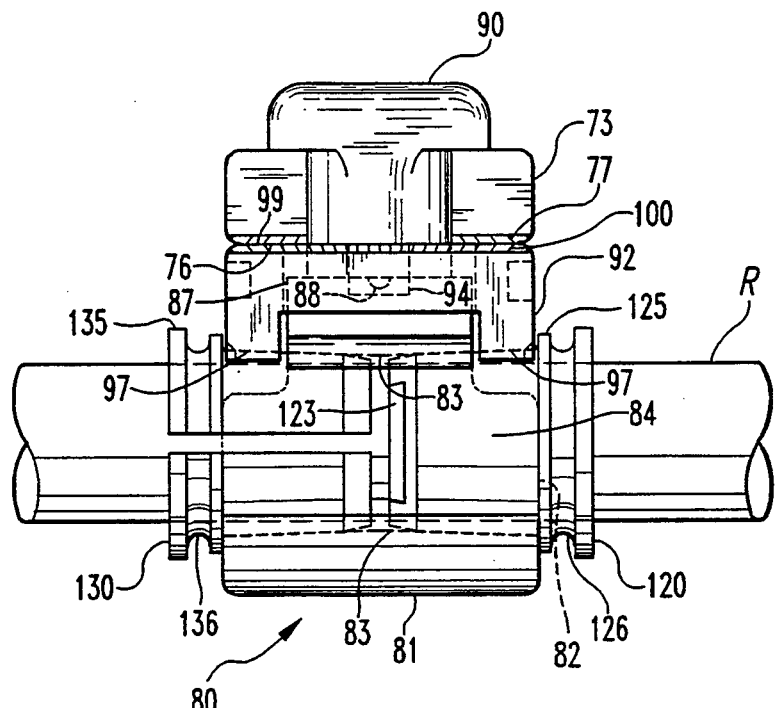
FIG. 18 shows top elevational view of the clamp assembly shown in FIG. 17 after insertion of the conical sleeves into the clamp channel, thereby clamping the spinal rod to the variable angle screws.

The washer 92 further includes a rod face 95 directed toward the rod channel 82. The rod face 95 defines a pair of rod engagement projections 96, themselves defining rod engaging grooves 97. Rod engaging grooves 97 are configured to receive a portion of the spinal rod therein as shown in FIGS. 17 and 18 and are further configured to be tapered away from the rod channel 82 complementary to the tapered portions 83 of the rod channel 82. In a preferred embodiment, tapered rod engaging grooves 97 are formed at a 2° slope in either direction away from the hub 87 and away from the rod channel. 82 as shown in FIGS. 17 and 18.

The washer 92 further includes an opposite outward face 99 that includes a plurality of radial splines 100 formed thereon. The radial splines 100 are configured comparable to the radial splines 77 on the variable angle screw 70 so that the face 76 of the screw 70 can be interdigitally engaged to outward washer face 99. The projection 89 can be circular in cross section so that the variable angle screw 70 can be rotated relative to the projection about its U-shaped slot 74. The washer 92 further includes a pair of slots 98 formed in opposite sides of the washer between the rod face 95 and outward washer face 99. Slots 98 are configured for engagement by a clamp insertion instrument so that the clamp assembly 80 may be easily maneuvered into place within a patient and connected to a variable angle screw 70 and spinal rod as hereinafter described.

Once staked onto the hub 87, the washer 92 can slide along the hub between the body 81 and the stake portions 88. It is contemplated that the maximum distance between the washer face 99 and the flat inward surface of the T-bar 91 when the staked recesses 94 are in contact with the staked portion 88 of the hub 87, is 0.144 inches. This dimensional relationship ensures that a variable angle screw having an upper yoke 73 thickness of 0.161 inches in accordance with the preferred embodiment, can be clamped between the washer 92 and T-bar 90.

In an important feature of this embodiment, conical sleeves are used in concert with the washer 92, circular projection 89, and T-bar 92 to attach the spinal rod R and variable angle screw 70 to the clamp assembly 80.

Figure 13:
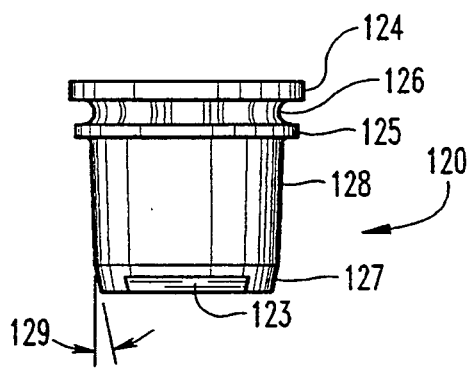
FIG. 13 is a top elevational view of one embodiment of a conical attachment sleeve to be used with the clamp assembly of FIG. 11.
Figure 14:
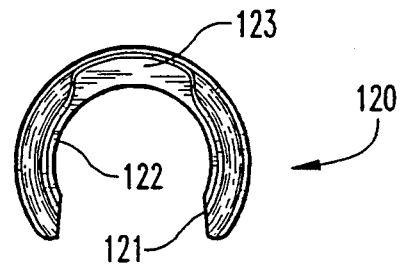
FIG. 14 is an end elevational view of the conical sleeve shown in FIG. 13.

FIGS. 13 and 14 show one embodiment of the conical sleeve 120, while FIGS. 15 and 16 show another embodiment denoted as sleeve 130. Both conical sleeves 120 and 130 are sized to loosely receive a spinal rod therethrough to freely slide along the rod surface. Conical sleeve 120 includes a gap 121 as shown in FIG. 14, that is sized so that the inner surface 122 can be pressed onto a spinal rod at any location along the rod. Conical sleeve 130 includes a longitudinal gap 131 as shown in FIG. 16, that is sized so as to require the sleeve 130 to be applied to a spinal rod from either end, and then pushed or pulled along the rod surface to a desired location.

Referring to FIG. 13, conical sleeve 120 includes a first flange 124 radially disposed at one end, a first tapered portion 127 at the opposite end and a second flange 125 radially disposed therebetween. The region between first flange 124 and second flange 125 defines a recess groove 126, and the region between the second flange 125 and first tapered portion 127 defines a second tapered portion 128. As shown in both FIGS. 13 and 14, sleeve 120 further includes a tab 123 located radially opposite to the channel 121 on the first tapered portion 127 and projecting generally perpendicular to the outer surface of sleeve 120. Referring to FIG. 15, conical sleeve 130 is provided with an identical first flange 134, recessed groove 136, second flange 135, first tapered portion 137, and second tapered portion 138.

The clamping of a spinal rod R and variable angle screw 70 by a clamp assembly 80 using conical sleeves 120 and 130 is shown in FIG. 17 and 18. In FIG. 17, the upper yoke 73 of the variable angle spinal screw 70 is shown as being engaged to the circular projection 89 between the inward surface 91 of the T-bar 90 and outward face 99 of the washer 92. The spinal rod R is shown as being received within the channel 82 and with conical sleeves 120 and 130 slidably disposed thereon. A sleeve compressing tool (not shown) is used to move conical sleeves 120 and 130 in the direction of arrows 140 and 141 respectively, and to thereby force the sleeves into the rod channel 82.

To facilitate initial entry of sleeves 120 and 130 into the channel 82, the first tapered surfaces 127 and 137 of sleeves 120 and 130, respectively, are sloped at a greater angle than the slope of tapered walls 83 of the channel 82. In the preferred embodiment, the first tapered surfaces 127 and 137 are sloped at an angle of 12° shown at 129 and 139 in FIGS. 13 and 15, respectively. The second tapered surfaces 128 and 138 of sleeves 120 and 130 are sloped complementary to tapered walls 83 of the rod channel 82. Thus, in a preferred embodiment, surfaces 128 and 138 are sloped 4° from the second flanges 125 and 135 toward the first tapered surfaces 127 and 137, respectively. As the sleeves 120 and 130 are forced into the rod channel 82, the sleeve gaps 121 and 131 become narrower, thereby creating greater resistance between the inner sleeve surfaces 122 and 132 and the spinal rod R. At the same time, tapered surfaces 128 and 138 create a friction fit with a complimentarily tapered walls 83 of the rod channel 82. When sleeves 120 and 130 are fully inserted so that the second flanges 125 and 135 are in contact with the clamp body 81 as shown in FIG. 18, the greatest resistance between the sleeve surfaces, the spinal rod and the clamp assembly 80 are achieved.

Insertion of the conical sleeves 120 and 130 to fix the clamp assembly 80 to the spinal rod R also acts to displace the washer 92 thereby fixing the variable screw 70 between the washer 92 and T-bar 90. As the conical sleeves are forced into the rod channel 82, tapered surfaces 128 and 138 contact the tapered rod engaging grooves 97 of the washer 92, thereby pushing the washer 92 towards the T-bar 90 as shown by arrows 142 in FIG. 17. When conical sleeves 120 and 130 are fully inserted, the washer 92 is displaced far enough in the direction of arrows 142 to clamp the variable angle screw 70 between the outward washer face 99 and the flat inward surface 91 of the T-bar 90.

Because of the width of the gap 121 in the conical sleeve 120, a potential problem exists in that the sleeve 120 may become rotated within the rod channel 82 so that the tapered surface 128 will not come in contact with the rod engaging groove 97 when the sleeve 120 is forced into the rod channel 82. For this reason, conical sleeve 120 is provided with an orientation tab 123 on the tapered surface 127 as shown in FIGS. 13 and 14. The sleeve 120 is configured so that as long as the tab 123 is visible within the channel opening 184, as shown in FIG. 18, the tapered surface 128 will contact the rod engaging groove 97 to properly act with the sleeve 130 to displace the washer 92. As the washer 92 engages the variable angle screw 70, the radial splines 100 on the outward washer face 99 interdigitate with the radial spline 77 on the interdigitating face 76 of the screw 70 to thereby fix the angulation of the screw 70 as shown in FIG. 18. Thus, insertion of the conical sleeves 120 and 130 into the rod channel 82, as shown in FIGS. 17 and 18, effectively clamps the channel rod R to the variable angle screw 70, wherein the screw 70 may be oriented at any angle with respect to the spinal rod.

Conical sleeves 120 and 130 are provided with recess grooves 126 and 136, respectively, to facilitate the removal of the sleeves from rod channel 82, if desired. Thus, if repositioning of the clamp assembly 80 is desired, conical sleeves 120 and 130 can be loosened and backed out of the rod channel 82 by engaging a sleeve remover (not shown) within recess grooves 126 and 136, and applying force in the direction opposite to clamp assembly 80, thereby sliding sleeves 120 and 130 out of the rod channel 82. Repositioning of clamp assembly 80 may then be accomplished and the spinal rod may be re-clamped to the variable angle screw using the procedure previously described.

Figure 19:
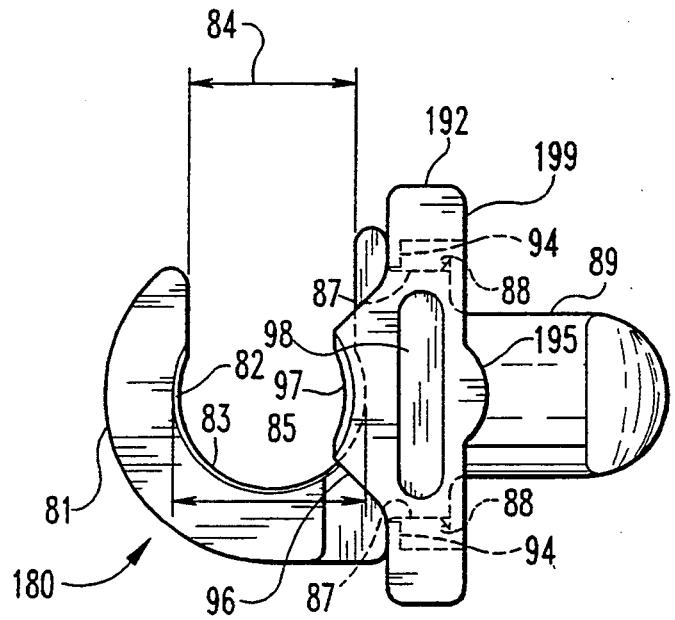
FIG. 19 is an end elevational view of a top-loading clamp assembly for use with a spinal hook and conical rod attachment sleeves, in accordance with another embodiment of the present invention.

FIG. 19 shows an alternate embodiment of a clamp assembly 180 which is identical to the clamp assembly 80 in all respects with the exception of the washer face 199 of the washer 192. Thus, the remaining portions of the clamp assembly 180 are identified using the same reference numbers previously used to identify the various components of the clamp assembly 80. As shown in FIG. 19, the washer face 199 of the clamp assembly 180 defines a vertebral fixation element engagement projection 195 configured to mate, for example, with the groove 16 of one side of the central post hook 10 shown in FIG. 4. The clamp assembly 180 contemplates that the spinal hook 10 will be firmly engaged between the washer 192 and the inward surface 91 of the T-bar 90 when the conical sleeves 120 and 130 are forcibly inserted into the rod channel 82 as previously described.

Figure 20:
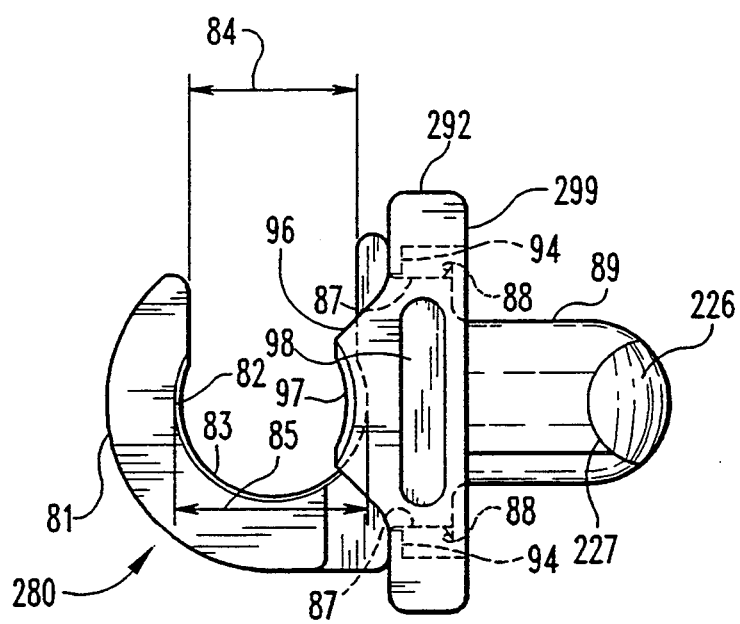
FIG. 20 is an end elevational view of a top-loading clamp assembly for use with a spinal hook and conical rod attachment sleeves, in accordance with a further embodiment of the present invention.

FIG. 20 shows a further alternate embodiment of a clamp assembly 280 which is also identical to the clamp assembly 80 in all respects with the exception of the washer face 299 of the washer 292 and the inward surface 227 of the T-bar 226. Thus, the remaining portions of the clamp assembly 280 are again identified using the same reference numbers previously used to identify the various components of the clamp assembly 80. As shown in FIG. 20, the washer face 299 of washer 292 is flat and lacks radial splines such as the radial splines 100 shown in FIG. 11. The inward surface 227 of the T-bar 226 is configured to mate, for example, with one of the coaxial grooves 16 in the post 14 of the central post hook 10 as shown in FIGS. 4 and 5. As with the previous embodiment, the clamp assembly 280 contemplates that the spinal hook 10 will be firmly engaged between the inward surface 227 of the T-bar 226 and the washer face 299 of the washer 292 when the conical sleeves 120 and 130 are forcibly inserted into the rod channel 82.

It can be appreciated from the description of the preferred embodiments that this invention provides novel means for clamping various spinal fixation elements to an elongated spinal rod. The clamp assemblies 20, 40, and 80 in accordance with this invention exhibit great versatility in making the connection between the fixation element and the spinal rod. The clamp assemblies 20 and 40 allow for top-tightening of the engagement between the spinal rod and the fixation element. In the case of the clamp assembly 20, a spinal hook can be tightened against a spinal rod by way of a top-tightening set screw 30 which presses against the spinal rod. In the clamp assembly 40, the top-tightening set screw 53 pushes against a spinal rod within the bore 42, which pushes against the washer 55, which finally presses the upper yoke 73 of a variable angle screw 70 between the spline face 63 and the inward face 49 of the T-bar 48. In the clamp assembly 80, conical sleeves 120 and 130 are forced into the rod channel 82, thereby fixing the spinal rod to the clamp assembly, and also pushing against the washer 92, which finally presses the upper yoke 73 of a variable angle screw 70 between the outward washer face 99 and the inward face 91 of the T-bar 90.

In the clamp assembly 180, conical sleeves 120 and 130 fix the spinal rod to the clamp assembly as previously described, and also push against the washer 192 to press the post 14 of a spinal hook 10 between the outward washer face 199 and the inward face 91 of the T-bar 90. In the clamp assembly 280, conical sleeves 120 and 130 fix the spinal rod to the clamp assembly as before, and also push against the washer 292 to press the post 14 of a spinal look 10 between the outward washer face 299 and the inward surface 227 of the T-bar 226.

While the invention has been illustrated and described in detail in the drawings and foregoing description, the same is to be considered as-illustrative and not restrictive in character, it being understood that only the preferred embodiments have been shown and described and that all changes and modifications that come within the spirit of the invention are desired to be protected.

What is claimed is:

1. A connector for securing a vertebral fixation element to a spinal rod, comprising:
   a body defining a channel configured to receive a spinal rod therethrough along a longitudinal axis of said channel;
   a projection extending from said body generally transverse to said longitudinal axis, said projection defining a clamping member having a clamping surface directed inwardly toward said channel
   a washer having a first surface and a second surface opposite said first surface, said washer further defining an opening for slidably receiving said projection therethrough when said washer is engaged to said body between said clamping surface and said channel; and
   means for forcing said washer toward said clamping member, said means residing in said channel and bearing against said first washer surface to engage and clamp the vertebral fixation element disposed between said clamping surface and said second washer surface.

2. The connector of claim 1, wherein:
   said body defines a hub between said channel and said projection, said hub having a shape complementary to said opening in said washer to prevent rotation of said washer about said hub when said washer is disposed thereon.

3. The connector of claim 2, including:
   at least one staking recess defined in said second washer surface adjacent said opening; and
   a staked portion of said hub projecting outward therefrom for engagement within said staking recess when said washer is disposed on said hub;
   whereby said washer is inhibited by said staked portion from sliding toward said clamping member more than a predetermined distance from said channel.

4. The connector of claim 3, wherein said first surface of said washer further includes:
   a number of rod engaging grooves configured to receive a portion of the spinal rod therein.

5. The connector of claim 3, wherein said channel is an elongated bore extending through said body.

6. The connector of claim 5, wherein said means for forcing includes a threaded set screw having a tip configured for bearing against the spinal rod when the rod extends through said elongated bore.

7. The connector of claim 3, wherein said first surface of said washer further includes:
   a number of rod engaging projections, each of said rod engaging projections defining a rod engaging groove configured to receive said forcing means therein.

8. The connector of claim 7, wherein said channel includes a channel opening extending through said body and into said channel, said channel opening further extending along the length of said channel.

9. The connector of claim 8, wherein said channel opening is sized to receive the spinal rod therethrough.

10. The connector of claim 9, wherein said channel further includes:
    two end portions, each of said end portions having a first predetermined length along said longitudinal axis; and
    a center portion having a second predetermined length along said longitudinal axis,
    wherein said first predetermined length is greater than said second predetermined length and said channel is linearly tapered from said first two end portions toward said center portion.

11. The connector of claim 10, wherein said elongated channel is tapered at a rate of 4 degrees from said end portions toward said center portion.

12. The connector of claim 11, wherein said means for forcing includes a pair of conical sleeves configured to receive the spinal rod therethrough, and being further configured to be received within said channel with a predetermined fit,
    wherein the spinal rod is clamped within said channel when said conical sleeves are forced into said channel.

13. The connector of claim 1, wherein said clamping member includes a T-bar.

14. The connector of claim 13, wherein said T-bar is arranged generally parallel to the longitudinal axis of said channel.

15. The connector of claim 14, wherein said clamping surface of said T-bar is substantially flat.

16. The connector of claim 15, wherein said second surface of said washer includes a plurality of radial splines adapted for interdigitating engagement with a surface of the fixation element having complementary radial splines.

17. The connector of claim 15, wherein said second surface of said washer includes at least one convexly curved projection configured to be received within a groove in the vertebral fixation element.

18. The connector of claim 14, wherein said clamping surface of said T-bar is convexly curved to be received within a groove in the vertebral fixation element.

19. The connector of claim 18, wherein said second surface of said washer is substantially flat.

20. A connector for securing a vertebral fixation element to a spinal rod, comprising:
   a body defining a channel configured to receive a spinal rod therethrough along a longitudinal axis of said channel, said body defining a channel opening extending through said body and into said channel, said channel opening further extending axially along the length off said channel;
   a projection extending from said body generally transverse to said longitudinal axis, said projection defining a clamping member having a clamping surface directed inwardly toward said body;
   a pair of conical sleeves configured to receive the spinal rod therethrough, and being further configured to be received within said channel with a predetermined fit; and
   a washer having a first surface configured to engage said conical sleeves, and a second surface opposite said first surface, said washer being disposed between said channel, and said clamping surface of said clamping member,
   wherein said clamping surface and said second washer surface are configured to engage opposite surfaces of the vertebral fixation element disposed between said clamping member and said washer.

21. The connector of claim 20, wherein each of said conical sleeve comprises:
   a first end having a first flange disposed radially thereon;
   a second end opposite said first end, said second end defining a first tapered portion adjacent thereto;
   a second flange disposed between said first end and said second end, said flanges defining a recess therebetween;
   a body defining a second tapered portion between said first tapered portion and said second flange; and
   a lengthwise slit extending through said sleeve, wherein said sleeve is hollow and sized to receive a spinal rod therethrough with a predetermined fit.

22. The connector of claim 21, wherein said slit is sized to permit said sleeve to receive the spinal rod through said slit.

23. The connector of claim 22, further comprising:
   a tab radially disposed on said first tapered portion adjacent said second end and radially opposite said slit, said tab being sized to restrict axial rotation of said sleeve when said sleeve is disposed within said channel and said tab is disposed within said channel opening.

24. The connector of claim 21, wherein said slit is sized to require said sleeve to receive the spinal rod through either of said ends.

25. The connector of claim 21, wherein said first tapered portion is tapered 12 degrees throughout its length.

26. The connector of claim 25, wherein said second tapered portion is tapered 4 degrees throughout its length.

27. A spinal fixation system for engagement to the spine of a patient between several vertebral levels, comprising:
   an elongated spinal rod configured for placement adjacent the spine of a patient spanning several vertebral levels, said rod defining a longitudinal rod axis along its length;
   a vertebral fixation element including;
      a vertebra engaging portion; and
      a rod engaging portion formed by a number of posts extending from said vertebra engaging portion, said posts defining a slot opening therebetween and said posts each having opposite lateral surfaces configured to engage said spinal rod; and
   a top-loading clamp for clamping said vertebral fixation element to said spinal rod, including;
      a body defining a channel configured to receive a spinal rod therethrough along a longitudinal axis of said channel, said groove further extending axially along the length of said channel;
      a projection extending from said body generally transverse to said longitudinal axis, said projection defining a clamping member having a clamping surface directed inwardly toward said body;
      a pair of conical sleeves configured to receive the spinal rod therethrough, and being further configured to be received within said channel with a predetermined fit; and
      a washer having a first surface configured to engage the spinal rod, and a second surface opposite said first surface, said washer being disposed between said channel and said clamping surface of said clamping member,
   wherein said clamping surface and said second washer surface are configured to engage opposite surfaces of the vertebral fixation element disposed between said clamping member and said washer.

28. A connector for clamping a vertebral fixation element to a spinal rod, comprising:
   a body defining a channel configured to receive a spinal rod therethrough along a longitudinal axis of said channel, said body having a surface defining at least one threaded bore extending into said body and intersecting said channel;
   a projection extending from said body generally transverse to said longitudinal axis and defining a clamping surface directed inwardly toward said channel, said projection being configured to receive a portion of the vertebral fixation element between the spinal rod and said clamping surface; and
   a threaded set screw adapted to be received within said threaded bore, and contact the spinal rod when said set screw is threaded into said threaded bore and the rod is disposed within said channel, wherein the spinal rod bears against said portion of the vertebral fixation element to clamp said portion between the rod and said clamping surface thereby restraining relative movement between the spinal rod and the vertebral fixation element.

29. The connector of claim 28, wherein said clamping surface includes a T-bar arranged generally parallel to said longitudinal axis of said rod channel, said T-bar having said clamping surface directed inwardly toward said elongated bore, said clamping surface configured to engage a complementarily configured surface of the vertebral fixation element disposed between the spinal rod and said T-bar.

30. The connector of claim 29, wherein said clamping surface of said T-bar is convexly curved to be received within a groove in the vertebral fixation element.

31. The connector of claim 30, wherein:

said body includes a top surface defining a first threaded bore therethrough from said top surface intersecting said channel, whereby said set screw can be threaded into said first threaded bore to clamp said spinal rod within said channel.

32. The connector of claim 31, wherein:

said body includes a bottom surface opposite said top surface and further defines a second threaded bore therethrough from said bottom surface intersecting said channel, whereby said set screw can be threaded alternatively into said first threaded bore or said second threaded bore to clamp said spinal rod within said channel.

33. The connector of claim 32, wherein said first threaded bore intersects said rod bore at an angle between 60° and 90°.

* * * * *

UNITED STATES PATENT AND TRADEMARK OFFICE
CERTIFICATE OF CORRECTION

PATENT NO. : 5,423,818

DATED : June 13, 1995

INVENTOR(S) : VAN HOECK ET AL.

It is certified that error appears in the above-identified patent and that said Letters Patent is hereby corrected as shown below:

Column 3, line 46, "THE" should be changed to "the".

Column 5, line 41 "*" should be deleted.

Column 7, line 19, "hip" should be changed to "tip".

Column 8, line 1, ":" should be deleted.

Column 8, line 1, "," should be changed to ".".

Column 8, line 25, "wherein" should be changed to "therein".

Column 13, line 49, "as-illustrated" should be changed to "as illustrative".

Signed and Sealed this

Fourteenth Day of November, 1995

*Attest:*

BRUCE LEHMAN

*Attesting Officer*  *Commissioner of Patents and Trademarks*